US010239892B2

(12) United States Patent
Sundermeyer et al.

(10) Patent No.: US 10,239,892 B2
(45) Date of Patent: *Mar. 26, 2019

(54) METHOD FOR PRODUCING ALKYL-INDIUM COMPOUNDS AND THE USE THEREOF

(71) Applicant: UMICORE AG & CO. KG, Hanau-Wolfgang (DE)

(72) Inventors: Joerg Sundermeyer, Marburg (DE); Annika Frey, Hanau (DE); Wolf Schorn, Giessen (DE); Ralf Karch, Kleinostheim (DE); Andreas Rivas-Nass, Schriesheim (DE); Eileen Woerner, Nidderau (DE); Angelino Doppiu, Seligenstadt (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/460,816

(22) Filed: Mar. 16, 2017

(65) Prior Publication Data
US 2017/0183361 A1 Jun. 29, 2017

Related U.S. Application Data

(63) Continuation of application No. 14/913,058, filed as application No. PCT/EP2014/067547 on Aug. 18, 2014, now Pat. No. 9,617,284.

(30) Foreign Application Priority Data

Aug. 22, 2013 (DE) .......... 10 2013 216 637
Aug. 8, 2014 (DE) .......... 10 2014 111 376

(51) Int. Cl.
*C07F 5/00* (2006.01)
(52) U.S. Cl.
CPC ..................... *C07F 5/00* (2013.01)
(58) Field of Classification Search
CPC ................... C07F 5/00; C07F 5/003
See application file for complete search history.

(56) References Cited

U.S. PATENT DOCUMENTS

| | | | |
|---|---|---|---|
| 4,847,399 A | 7/1989 | Hallock et al. | |
| 5,380,895 A | 1/1995 | Krafft | |
| 5,663,390 A * | 9/1997 | Giolando ............ | C07F 5/00 556/1 |
| 5,817,847 A | 10/1998 | Giolando | |
| 5,886,203 A | 3/1999 | Jones et al. | |
| 5,980,978 A | 11/1999 | Jones et al. | |
| 6,680,397 B2 | 1/2004 | Shenai-Khatkhate et al. | |
| 7,166,734 B2 * | 1/2007 | Shenai-Khatkhate .... | C07F 3/00 556/1 |
| 8,513,447 B1 | 8/2013 | Maggiarosa et al. | |
| 9,540,401 B2 | 1/2017 | Sundermeyer et al. | |
| 9,617,284 B2 * | 4/2017 | Sundermeyer ............ | C07F 5/00 |

FOREIGN PATENT DOCUMENTS

| | | |
|---|---|---|
| CN | 1156996 A | 8/1997 |
| CN | 1410428 A | 4/2003 |
| CN | 1445230 A | 10/2003 |
| DE | 37 42 525 A1 | 6/1989 |
| EP | 0 372 138 A1 | 12/1988 |
| JP | H02-184690 A | 7/1990 |
| JP | H02-502464 A | 8/1990 |
| JP | H11-514677 A | 12/1999 |
| JP | 2003-252878 A | 9/2003 |
| JP | 2006-104189 A | 4/2006 |
| KR | 101221861 B1 | 1/2013 |
| WO | 89/05303 A1 | 6/1989 |
| WO | 2013/083449 | 6/2013 |
| WO | 2015/024893 A1 | 2/2015 |

OTHER PUBLICATIONS

International Search Report for PCT/EP2014/067547, dated Nov. 13, 2014 in English and German Language.
Gynane, M. J. S, Waterworth, L. G. und Worrall, I. J., J. "Preliminary Communication: Formation of Methyl-and Ethylgallium Halides by the Direct Reaction Between the Metal and Alkyl Halide" Journal of Organometallic Chemistry, 40, 1972, C59-C60.
Gynane, M. J. S, Waterworth, L. G. und Worrall, I. J., J. "Preliminary Communication: The Synthesis of Lower Alkylindium Halides by the Direct Reaction Between the Metal and Alkyl Halides" Journal of Organometallic Chemistry, 40, 1972, C9-C10.
Gynane, M. J. S, Waterworkth, L. G. und Worrall, I. J., J. "Oxidative Addition Reactions of Group III Metals in Low Oxidation States: III*. Reaction s of Indium Monohalides with Alkyl Halides" Journal of Organometallic Chemistry, 43, 1972, 257-264.
Stoll S L, et al: "Selenide and Selenolate Compounds of Indium: A Comparative Study of In—Se Bond-Forming Reactions", Journal of the Chemical Society, Dalton Transactions, Chemical Society. Letchworth, GB, Jan. 1, 1997, pp. 1315-1321, SP001146779.

(Continued)

Primary Examiner — Pancham Bakshi
(74) Attorney, Agent, or Firm — Smith, Gambrell & Russell, LLP

(57) ABSTRACT

The invention relates to a method for the cost-effective and environmentally friendly production of alkyl indium sesquichloride in high yield and with high selectivity and purity. The alkyl indium sesquichloride produced according to the invention is particularly suitable, also as a result of the high purity and yield, for the production, on demand, of indium-containing precursors in high yield and with high selectivity and purity. As a result of the high purity, the indium-containing precursors that can be produced are particularly suitable for metal organic chemical vapor deposition (MOCVD) or metal organic vapor phase epitaxy (MOVPE). The novel method according to the invention is characterized by the improved execution of the method, in particular a rapid process control. Owing to targeted and extensive use of raw materials that are cost-effective and have a low environmental impact, the method is also suitable for use on an industrial scale.

16 Claims, No Drawings

(56) References Cited

OTHER PUBLICATIONS

Konrad Koszinowski: "Oxidation State, Aggregation, and Heterolytic Dissociation of Allyl Indium Reagents", Journal of the American Chemical Society, vol. 132, No. 17, May 5, 2010, pp. 6032-6040, XP55151064.
Bähr, Burba: Organo-Indium-Verbindungen. y: Houben-Weyl, 1970. 350.
Schöllkopf: Li-organische Verbindungen, y: Houben-Weyl, 1970. 134.
International Preliminary Report on Patentability dated Feb. 23, 2016 received in International application No. PCT/EP2014/067547; 12 pages (in German with English Translation).
Written Opinion of the International Searching Authority dated Feb. 26, 2015 received in International application No. PCT/EP2014/067547; 10 pages (in German with English Translation).
Chinese Search Report dated Dec. 23, 2016 for CN 201480046316.2 (2 pages).
First Chinese Office Action dated Jan. 11, 2017 for CN 201480046316.2 (5 pages in Chinese with English machine translation).
Second Chinese Office Action dated Sep. 26, 2017 for CN 201480046316.2 (3 pgs. in Chinese with English machine translation).
Chinese Search Report dated Dec. 29, 2016 for CN 201480046319.6 (1 pg.).
First Chinese Office Action dated Feb. 27, 2017 for CN 201480046319.6 (5 pgs. in Chinese with English machine translation).
Second Chinese Office Action dated Nov. 17, 2017 for CN 201480046319.6 (3 pgs. in Chinese with English machine translation).
Japanese Office Action dated Jul. 23, 2019 for JP2016-535444 (7 pgs. in Japanese with English machine translation).

\* cited by examiner

METHOD FOR PRODUCING ALKYL-INDIUM COMPOUNDS AND THE USE THEREOF

The invention provides a process for preparing alkylindium sesquichloride, characterized by the general formula $R_3In_2Cl_3$ (also referred to hereinafter as compound (A)) in high yield and with high selectivity and purity.

The alkylindium sesquichloride prepared in accordance with the invention is particularly suitable, because of its high purity and yield as well, for preparation of indium-containing precursors in accordance with demand, preferably those of the general formula $R_3In$ (also referred to hereinafter as compound (B)) or $R_2InR'$ (also referred to hereinafter as compound (C)). The indium-containing precursors obtainable with high yield and in high purity from compound (A) are particularly suitable for metal-organic chemical vapour deposition (MOCVD), also known as metal-organic chemical vapour phase epitaxy (MOVPE).

Where the term "process" is used in accordance with this invention, this always means the process for preparing the compound (A) and the optional process for preparing indium-containing precursors, preferably of the compounds (B) or (C), which follows on.

PRIOR ART

The prior art describes various processes for preparing compounds which are typically used as organometallic precursors for MOCVD processes, i.e. the starting materials thereof, referred to hereinafter in simplified form as "precursor starting material".

"Precursor starting materials" in the context of this invention are those which can be converted by further reaction steps to the actual organometallic precursors (referred to as "precursors" or "indium-containing precursors" for short), which can then be used directly in MOCVD processes. It is advantageous here to provide such precursor starting materials or to prepare precursors by those precursor starting materials which are themselves obtainable with high selectivity and yield. In addition, it can be very advantageous to provide precursor starting materials which are preparable in a simple manner and with high purity and may be isolable and of sufficient storage stability to enable very rapid preparation of high-purity precursors for MOCVD processes in accordance with demand. The MOCVD processes are especially used in the production of semiconductor layers for optoelectronic applications such as solar cells or LEDs, but also for production of layers in other fields of use, which typically requires ultra-high purity of the particular precursor used, and the absence or the presence of only very small proportions of oxygen-containing impurities in particular.

For instance, there are various known processes for preparing, for example, indium-containing, gallium-containing or else aluminium-containing precursors or corresponding precursor starting materials. However, the respective process conditions are not necessarily transferable, or cannot be transferred unchanged, between the elements. It should be taken into account that the elements aluminium, gallium and indium already exhibit different chemical behaviour, which regularly results in the need for a particular tailored process regime in production of respective precursors.

Processes known in the prior art for preparing indium-containing precursors or precursor starting materials often encounter considerable difficulties with regard to preparation in the purity and amount required for customary uses, particularly also at acceptable cost. For instance, the electrical properties of the semiconductor layers produced from indium-containing precursors by MOCVD can be considerably impaired by impurities in the precursors or precursor starting materials. Numerous preparation processes are additionally very time-consuming. In addition, frequently only low yields are achieved, and the reaction steps are frequently characterized by a reduced selectivity. Because of the use of organic solvents as well in known preparation processes for preparing indium-containing precursors or precursor starting materials, the processes are usually costly and not very environmentally friendly, and can be associated with solvent residues in the intermediates and the end products, which in turn considerably restrict the use thereof or necessitate a costly and inconvenient purification.

DE 37 42 525 A1 relates to a process for preparing metal alkyls such as trimethylindium, and describes a preparation proceeding from lithium tetramethylindate as precursor starting material by reaction with indium trichloride in an organic solvent. A mixture comprising trimethylindium is obtained, and the latter subsequently still has to be isolated and purified. Even after purification, the yield is reported as only 82% of the theoretical value. The preparation is also characterized by a relatively high process duration of more than 24 hours.

EP 0 372 138 A1 describes a process for preparing organometallic compounds, by which trialkylindium compounds too are obtainable via a nonvolatile precursor starting material which may, for example, be lithium tetramethylindate. The preparation of lithium tetramethylindate from indium trichloride takes place in diethyl ether with addition of methyllithium, which makes the process very costly overall. The lithium tetramethylindate is reacted with indium trichloride to give trimethylindium, which subsequently still has to be purified. No figures are given for the actual yield. Moreover, the process described is very costly and inconvenient, one reason being the numerous isolation and purification steps.

Gynane et. al. describe the reaction of indium with alkyl bromides and alkyl iodides to give sesquihalides (Gynane, M. J. S., Waterworth, L. G. and Worrall, I. J., J. Organometal. Chem., 40, 1972). A further publication also describes the reaction of indium monobromide or indium monoiodide with alkyl iodides or alkyl bromides to give alkylindium dihalides, but very long reaction times are required (Gynane, M. J. S., Waterworth, L. G. and Worrall, I. J., J. Organometal. Chem., 43, 1972).

U.S. Pat. No. 5,663,390 relates to the preparation of alkyl metal chlorides by reaction of an alkyl chloride with elemental metal in the presence of $H_2$ as reaction accelerator. The latter, however, is disadvantageous; more particularly, the process described is very complex and the conversion is only incomplete. The reaction overall is very inconvenient and costly, and is therefore unsuitable for the industrial scale.

Problem

The problem addressed by the present invention is that of providing a process which enables inexpensive preparation, in accordance with demand, of suitable precursor starting materials for indium-containing precursors, combined with a simple and rapid process regime. The process is also to enable the preparation of such compounds with high yield and high purity. The precursor starting materials should additionally be isolable in a simple manner and have sufficient storage stability.

In addition, indium-containing precursors obtainable from the starting material are to be very substantially free of oxygen impurities, and are to be obtainable in high yield and with high selectivity and purity proceeding from the starting material. As a result, the indium-containing precursors obtainable are to be particularly suitable for MOCVD processes, which requires high-purity organoindium compounds in each case for the production of semiconductor layers.

The process is additionally to be performable with a low level of environmental pollution and with low resource intensity.

Solution

The problem addressed by the present invention is solved by the subject-matter of the claims.

The problem is especially solved by a novel process for preparing alkylindium sesquichloride (compound (A)) having the general formula:

$$R_3In_2Cl_3$$

where R is a lower alkyl radical, i.e. one having 1 to 4 carbon atoms. The alkyl radical may be branched or unbranched, preferably unbranched. Suitable alkyl radicals are therefore isopropyl, cyclopropyl, isobutyl, sec-butyl, tert-butyl, but especially propyl, n-butyl and ethyl or methyl.

The structure of the compound (A) is yet to be finally clarified and may, instead of the above-specified formula $R_3In_2Cl_3$, also be regarded as a mixture of $R_2InCl$ and $RInCl_2$. It is also possible that these compounds are in equilibrium with one another and/or with $R_3In_2Cl_3$. The ratio of $R_2InCl$ and $RInCl_2$ to one another need not necessarily be 50:50, but may also vary in a ratio of generally about 40:60 to about 60:40.

Because of the starting substances used and further reagents used, the process is inexpensive and causes a low level of environmental pollution, and enables the preparation of $R_3In_2Cl_3$ with a rapid process regime and high yield, and with high purity. More particularly, it is possible in accordance with the invention to dispense with the use of organic solvents that are typically required, which contributes to a cost-effective and environmentally responsible process regime. It is additionally advantageous that compound (A) is isolable in a simple manner and has sufficient storage stability. Secondly, compound (A) is also amenable to further reaction steps without isolation, such that there is the possibility of developing inexpensive multistage reactions without inconvenient intermediate isolation ("one-pot reaction").

The process according to the invention is particularly suitable for preparing methylindium sesquichloride ($Me_3In_2Cl_3$) and ethylindium sesquichloride ($Et_3In_2Cl_3$), or mixtures of $Me_2InCl/MeInCl_2$ and $Et_2InCl/EtInCl_2$ (in some cases also in non-stoichiometric ratios), very particularly for the preparation of $Me_3In_2Cl_3$. R is thus preferably selected from ethyl and methyl; most preferably, R is methyl. Methyl and ethyl are abbreviated hereinafter to Me for methyl and Et for ethyl.

First of all, the invention thus provides a novel process for preparing $R_3In_2Cl_3$, i.e. the compound (A), as precursor starting material. The process according to the invention may be followed by further reaction steps, such that indium-containing precursors for MOCVD processes are also obtainable in accordance with the invention inexpensively and with a rapid process regime, and in high yield and purity. The process according to the invention thus comprises the preparation of compound (A). In embodiments, the process according to the invention may be followed by additional reaction steps for preparation of indium-containing precursors.

The indium-containing precursors are preferably selected from compounds of the general formula $R_3In$ (i.e. compound (B)) and $R_2InR'$ (i.e. compound (C)). Because of the process regime, in accordance with the invention, R is the same in compounds (A), (B) and (C); R' may be different from this, as detailed further down.

According to the invention, indium-containing precursors of the general formula:

$$R_3In$$

are those in which R is a lower alkyl radical having 1 to 4 carbon atoms. The alkyl radical may be branched or unbranched, preferably unbranched. R is especially selected from ethyl and methyl; in particular, R is methyl.

According to the invention, indium-containing precursors of the general formula:

$$R_2InR'$$

are those in which R is a lower alkyl radical having 1 to 4 carbon atoms, which may be branched or unbranched, and where R' is a nucleophilic radical other than R. R' is preferably selected from branched or unbranched and substituted or unsubstituted alkyl, branched or unbranched and substituted or unsubstituted aryl. R' may especially be alkyl or phenyl substituted by branched or unbranched alkyl or alkoxy groups, or alkyl or phenyl substituted by amine radicals. In particular, R' is alkyl or aryl radicals having 1 to 6 carbon atoms, substituted by branched or unbranched alkyl or alkoxy groups, such as methyl, ethyl, n-butyl, propyl, sec-butyl, tert-butyl, isobutyl, isopropyl, cyclopropyl, cyclobutyl, methoxy, ethoxy, n-butoxy, propoxy, sec-butoxy, tert-butoxy, isobutoxy, isopropoxy, cyclopropoxy, cyclobutoxy, or else alkyl or aryl radicals which have 1 to 6 carbon atoms and are substituted (especially mono- or disubstituted) by amine radicals, themselves substituted by radicals of the branched or unbranched alkyl group type, such as methyl, ethyl, n-butyl, propyl, sec-butyl, tert-butyl, isobutyl, isopropyl, cyclopropyl, cyclobutyl.

The nucleophilic R' radical may, for example, be phenyl, tolyl, mesityl, dimethylamino, diethylamino, dibutylamino, diisopropylamino, $Et_2N$—$(CH_2)_3$, $Me_2N$—$(CH_2)_2$, $Me_2N$—$CH_2$, $Et_2N$—$(CH_2)_2$, $Et_2N$—$CH_2$, isopropyl, cyclopropyl, isobutyl, sec-butyl, tert-butyl, cyclopropyl, but especially propyl, n-butyl and ethyl or methyl. If the definitions of R and R' encompass the same radicals, R and R' in compound (C) must differ from one another. Thus, for example, if R is methyl, R' must not be methyl.

In one embodiment of the invention, R is methyl and R' is an $Me_2N$—$(CH_2)_3$-radical. In a further embodiment of the invention, R is methyl and R' is ethyl. In a further embodiment of the invention, R is ethyl and R' is methyl. This results in the compounds $Me_2InEt$, $Et_2InMe$ and $Me_2In$—$(CH_2)_3$—$N$-$Me_2$ or $(CH_3)_2In$—$(CH_2)_3$—$N$—$(CH_3)_2$. In this embodiment, further reaction steps thus follow the process according to the invention, and so indium-containing precursors, preferably $R_3In$ (i.e. compound (B)) or $R_2InR'$ (i.e. compound (C)), can also be obtained inexpensively and in accordance with demand, and with a rapid process regime.

The indium-containing precursors (B) and (C) obtainable with preference from compound (A), because of their particularly high purity, are particularly suitable for the preparation of indium-containing layers films used in the semiconductor industry and produced in MOCVD processes, such as InP, InAlP and AlInGaP layers.

1. Process for Preparing Compound (A)

The process according to the invention for preparing $R_3In_2Cl_3$, i.e. compound (A), comprises the reaction steps of:

a1) reacting indium with an alkyl donor to form compound (A) in the presence of an activator, the alkyl donor being an alkyl chloride (RCl), and a2) optionally isolating the compound (A).

Reaction Step a1):

The indium can be used in a purity of preferably at least 5N or higher (corresponding to metallic purity >99.999% based on indium), but also as 4N (metallic purity=99.99%) indium. In principle, however, it is also possible to use indium of lower purity. The particle size may vary within wide limits, since the indium is in molten form at a reaction temperature (melting point of indium about 156° C.). For simpler measurement of the amounts required and filling of the reactor, it is possible, for example, to use granules having a particle size of 1 mm to 10 mm, especially of 4 mm to 6 mm (for example what are called indium shots of size about 0.5 cm), but it is also possible to use powder or even ingots.

The alkyl donor is a compound comprising an alkyl group, the alkyl donor being an alkyl halide where alkyl is as defined above and chlorine, bromine or iodine can be used as halide, especially chlorine. The alkyl donor may therefore especially be an alkyl chloride which thus, as well as the alkyl group, also comprises at least one chlorine atom. More particularly, the alkyl donor is an alkyl halide (especially an alkyl chloride) where alkyl is as defined above (see definition of R); more preferably, alkyl is methyl or ethyl, especially methyl. In preferred embodiments, the alkyl donor is thus methyl chloride (chloromethane) or ethyl chloride (chloroethane), more preferably methyl chloride.

Preference is given to using 1.5 to 5 equivalents of alkyl donor per equivalent of indium for this reaction, or 1.5 to 4.5 equivalents or 1.5 to 4 equivalents of alkyl donor per equivalent of indium, especially from 1.5 to 3 or 1.5 to 2.5 or 1.5 to 2.9 equivalents of alkyl donor per equivalent of indium. If the alkyl donor is used in too low a proportion in relation to the indium, there is the risk of incomplete conversion and a reduced yield of compound (A). If excessively high amounts of alkyl donor are used in relation to the indium, the process becomes too expensive and too uneconomic overall, and is no longer performable in an economically viable manner on the industrial scale, which is undesirable.

It has been found to be particularly advantageous to use between 1.5 and 4 equivalents of alkyl donor per equivalent of indium, even further preferably between 1.7 and 3 equivalents of alkyl donor per equivalent of indium and most preferably between 1.8 and 2.5 equivalents of alkyl donor per equivalent of indium. This makes it possible to achieve particularly high yields of compound (A).

Preference is given to adding the indium and the alkyl donor successively to the reaction vessel. More preferably, indium and activator are first initially charged and then the alkyl donor is added. This surprisingly led to high yields and additionally reduced the apparatus complexity. Thus, it is possible to simply weigh indium and activator into the reactor. Subsequently, the alkyl donor can be added in a controlled manner.

The addition of the alkyl donor to the indium is preferably effected by supplying the alkyl donor, which is preferably in gaseous form under standard conditions (boiling point of MeCl is −24° C., that of EtCl 12° C.), to the reaction through controlled continuous introduction of gaseous alkyl donor.

During introduction, over the course of the reaction, preferably as much alkyl donor as has been consumed is constantly replenished, such that the (positive) reaction pressure is kept constant. The control is effected, for example, automatically by means of a pressure sensor coupled to a metering valve.

Optionally, the alkyl donor can be added by condensing it in. If the alkyl donor is condensed in, the temperature during the addition is advantageously below 0° C. More preferably, a temperature of −20° C. is not exceeded during the addition of the alkyl donor. Preference is given to cooling from the outside in the course of addition of the alkyl donor. Preferably, the addition of the alkyl donor is effected by condensing it in at temperatures below 0° C., further preferably at temperatures of −260° C. to −20° C. (cooling with liquid nitrogen or dry ice). These figures apply only to the addition of the alkyl donor by condensing it in, which is optional. The alkyl donor is preferably condensed in under reduced pressure at a residual gas pressure of preferably below 1 hPa, preferably below 0.1 hPa and more preferably at not more than $5\times10^{-2}$ hPa. The subsequent heating of the reaction mixture establishes a gauge pressure of up to 15 bar, especially of 0.2 to 1.5 MPa, preferably 0.5 to 1 MPa and even more preferably between 0.6 and 1 MPa in the reaction vessel, these conditions being advisable only when the alkyl donor is being condensed in.

Preferably, the alkyl donor is introduced into the reactor in gaseous form. If the addition of the alkyl donor is effected by injection or continuous introduction, the total amount of alkyl donor required is generally not added from the start, as is the case when it is condensed in; instead, alkyl donor is permanently metered into the indium-activator mixture until the conversion is complete.

Optionally, however, the alkyl donor can also be introduced into the reactor in liquid form. This may be advantageous on the industrial scale, since no external heating of the alkyl chloride reservoir tank or a vaporizer unit is then needed to maintain a stable gas pressure of the alkyl donor, since chloromethane and chloroethane inter alia are sold as liquefied gas. The liquid alkyl donor can then be metered in under pressure directly from the liquefied gas tank. In the reactor, the alkyl donor evaporates immediately as a result of the reaction conditions that exist, and so the reaction with gaseous alkyl donor proceeds in the reactor.

The addition of the alkyl donor by introduction or injection generally commences at temperatures at or above 20° C. In one embodiment, the indium or the indium-activator mixture in the reactor is in liquid form on commencement of addition of the alkyl donor. Since pure indium has a melting point of 156.6° C., the addition then takes place at a temperature of 156° C. or more. Since the presence of the activator can lower the melting point of the initially charged indium mixture, the mixture may also already be liquid below 156° C. This means that, in this embodiment, indium and activator are initially charged and heated in the reactor until the mixture is liquid, and then introduction of the alkyl donor is commenced. Optionally, indium can also first be initially charged in the reactor, then heated until the indium is in liquid form, then the activator can be added and the addition of the alkyl donor can be commenced.

In another embodiment, the alkyl donor, for example the methyl chloride, is passed at room temperature into the reactor containing the initially charged indium-activator mixture and then heated to the desired reaction temperature, during which the introduction of alkyl donor is continued.

After commencement of the addition of the alkyl donor, the reaction mixture is heated up. A temperature of 250° C., preferably of 235° C., is preferably not exceeded here, in order to avoid side reactions, and for economic reasons too. At reaction temperatures above 235° C., a gradual thermal breakdown may be observed, which probably forms indium as a breakdown product. Preference is given to heating to temperatures of at least 150° C., further preferably at least 170° C. and more preferably 180° C., in order to enable particularly complete conversion to compound (A). The reaction temperatures are thus within the range from about 150° C. to about 250° C., or from 170° C. to 235° C., or from 180° C. to 230° C., irrespective of the manner in which the alkyl donor has been added.

Reaction step a1) can be conducted under inert gas such as argon or nitrogen. However, it is possible to conduct the reaction without additional inert gas in a pure atmosphere of alkyl donor, for example methyl chloride or ethyl chloride, which has advantages.

In general, the alkyl donor is added at a defined constant pressure, for example at a gauge pressure of 1 bar to 4.5 bar, or at 1.5 bar to 4 bar (absolute pressure: 2 bar to 5.5 bar or 2.5 bar to 5 bar). The procedure here may be that a certain gauge pressure of alkyl donor (i.e., for example, ethyl chloride or methyl chloride), for example 3.5 bar, is defined. By means of a flow regulator, always as much alkyl donor (i.e., for example, ethyl chloride or methyl chloride) is replenished into the reactor as is consumed, such that the pressure in the reactor remains approximately constant, i.e., for example, at 4.5 bar (or the gauge pressure at 3.5 bar). If no alkyl donor (i.e., for example, ethyl chloride or methyl chloride) is being consumed any longer, the reaction has ended.

In the course of the reaction, an activator is added. The person skilled in the art knows what is meant by an activator, namely compounds which, typically in small amounts, contribute to acceleration of the reaction and conversion. Suitable activators are generally Lewis acids, for example indium halides $InX_3$ (where X may be chlorine, bromine or iodine), indium trichloride ($InCl_3$), aluminium trichloride ($AlCl_3$), copper chloride ($CuCl_2$), chlorine $Cl_2$, hydrogen chloride HCl, iron chloride $FeCl_3$, $(PtCl_4)^{2-}$, $PdCl_2$, oxides such as $In_2O$, $TiO_2$, $NiO_2$, $Fe_2O_3$ or $[P_nBu_4][InCl_4]$. It is suspected that lower-valency indium(I) compounds, such as InCl, form in situ from indium metal and the Lewis acids used, and these then react with the alkyl donor in an oxidative addition.

According to the present invention, however, it is advantageous when the activator is not an indium halide $InX_3$ where X may be chlorine, bromine or iodine, is not chlorine $Cl_2$, hydrogen chloride HCl, hydrogen $H_2$, iron chloride $FeCl_3$, $(PtCl^{2-}$, $PdCl_2$, indium trichloride ($InCl_3$), aluminium trichloride ($AlCl_3$) or copper chloride ($CuCl_2$), and is not an oxide, especially $In_2O$, $TiO_2$, $NiO_2$ or $Fe_2O_3$.

However, it has been found that, surprisingly, alkylindium sesquichloride ($R_3In_2Cl_3$), dialkylindium chloride ($R_2InCl$), alkylindium dichloride ($RInCl_2$), trialkylindium ($R_3In$) in a mixture with indium halide $InX_3$ (where X may be chlorine, bromine or iodine), such as indium trichloride ($InCl_3$) in particular, and mixtures thereof can likewise be used and are even better suited. This has the advantage that no other metals than indium, which would lead to troublesome impurities at a later stage, are present in the system. A particular advantage in the case of use of the alkylindium sesquichloride product itself as an activator is that it is then possible, in a simple reaction regime, to utilize residues of the reaction product in the reactor for activation of the next batch, and no additional chemicals are required aside from indium and the alkyl donor and the preparation of compound (A) can be conducted semicontinuously. It will be apparent to the person skilled in the art that it is also possible to use other alkylindium halides including alkylindium sesquihalide, dialkylindium halide, alkylindium dihalide and mixtures thereof, where the halide is selected from F, Br and I. However, the halide is more preferably chloride. The activator is therefore preferably selected from dialkylindium chloride ($R_2InCl$), alkylindium dichloride ($RInCl_2$), trialkylindium ($R_3In$) in a mixture with indium halide $InX_3$ (where X may be chlorine, bromine or iodine), especially indium trichloride ($InCl_3$), and mixtures thereof, where R is as defined above. It is also possible to use mixtures.

In one configuration of the invention, the activator is added to the indium before commencement of the addition of the alkyl donor. The activator is preferably used in such an amount that the molar ratio of indium to activator is at least 4:1, further preferably at least 5:1, preferably at least 6:1 and even more preferably more than 8:1. If the amount of activator is too high, there is the risk of incomplete conversion to compound A. The molar ratio of indium to activator is preferably at most 300:1, more preferably at most 250:1 and even more preferably at most 200:1. Particularly advantageous molar ratios of indium to activator are therefore in the range of >100:1, i.e. of about 110:1, 130:1 or 140:1. When the amounts of activator are too small, the risk may be that the effect of the activator is no longer sufficient. The molar ratio is understood to mean the ratio of the molar amount of indium to the molar amount of activator. Different activators have different optimal molar ratios to indium, which can be determined in a simple manner in a few manual tests; for example, it is possible to use indium trichloride and trimethylindium together in a ratio of 10:1 relative to indium; in the case of use of methylindium sesquichloride, in contrast, ratios in the region of about 20:1 have been found to be useful.

It is also possible to use two compounds which first react with one another to give the compound actually active as the activator, for example indium trichloride and trimethylindium, which react with one another to give indium sesquichloride, which then acts as activator. In this case, the molar ratio is of course based on the compound indium sesquichloride effective as activator and not on the indium trichloride and trimethylindium starting materials therefor.

It was surprisingly possible by the process according to the invention to achieve high yields of compound (A) even in the absence of organic solvents. It is thus possible to dispense with organic solvents in the reaction of the indium with the alkyl donor to form compound (A). Organic solvents are understood in accordance with the invention to mean carbonaceous, liquid substances. Absence of an organic solvent is understood in accordance with the invention to mean that no organic solvent is additionally used as reaction medium. This has the advantage that any possible organic contaminations in the compound (A) resulting from partial breakdown of the solvent are avoided. Furthermore, this allows the process to be conducted in a more environmentally responsible manner. Moreover, in the absence of organic solvents in step a1), a particularly high selectivity of the reaction was surprisingly recorded.

The reaction time in step a1) is preferably between 10 min and 30 hours. A reaction time of at least 15 min, further preferably of at least 30 min and even further preferably of at least 40 min has been found to be particularly advantageous in relation to the yield of compound (A). The reaction time is more preferably at most 28 hours, further preferably at most 12 hours. Excessively high reaction times lead to a very costly and uneconomic process.

In all embodiments of the process according to the invention, the following reaction, in schematic form, proceeds in reaction step a1):

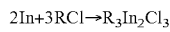

Reaction Step a2):

The isolation of compound (A), which is optional in accordance with the invention, preferably comprises the separation of volatile constituents from the reaction mixture present in the reaction vessel and/or process steps selected from the sublimation of the compound (A) from the reaction mixture and the mechanical removal of compound (A) from the reaction vessel. A simple variant of mechanical removal can be considered to be the discharge of the product in the liquid state.

The term "isolation" or "isolating" encompasses the separating of the particular desired reaction product from the reaction mixture present in the reaction vessel by removing the reaction product from the reaction vessel, or the removing of other compounds aside from the reaction product from the reaction mixture such that only the reaction product remains in the reaction vessel.

In one embodiment, compound (A) is isolated by withdrawal from the reaction vessel, which can be conducted with an aid such as a spoon, spatula, scraper, etc. Discharge in the liquid state is a very simple method, which can be brought about, for instance, by discharging by means of an appropriate valve or by using positive pressure to transfer the liquid into a vessel. It has been found to be particularly advantageous for the purity of the compound (A) first to separate volatile secondary constituents from the mixture present in the reaction vessel, especially alkyl donor such as RCl still present, i.e., for example, methyl chloride or ethyl chloride, and only subsequently to withdraw the compound (A) from the reaction vessel. Volatile secondary constituents, especially alkyl donor RCl still present, are preferably separated by application of vacuum. In this case, a vacuum with a residual gas pressure below 1 hPa, further preferably below 0.1 hPa, has been found to be useful.

Optionally, the isolation of the compound (A) may be followed by further steps to purify the compound (A), suitable processes for purifying chemical substances being known to those skilled in the art. Preferably in accordance with the invention, through the particular process regime and the inventive reactants, however, a sufficiently high purity of the compound (A) is achieved even without further purification steps. Preferably in accordance with the invention, therefore, aside from the preferred isolation from compound (A), i.e. the separation of volatile secondary constituents and withdrawal of compound (A) from the reaction vessel, no further steps to purify the compound (A) are required.

In one embodiment, during the isolation of compound (A), there is only incomplete withdrawal of the reaction product from the reaction vessel. The residues of compound (A) remaining in the reaction vessel, after addition of further indium and another addition of alkyl donor as activator, are utilized for the further preparation of compound (A) in the next batch.

In alternative embodiments, compound (A) is not isolated from the reaction mixture. In such embodiments, the reaction mixture comprising compound (A) is used directly for preparation of indium-containing precursors, especially compound (B) or (C). In these embodiments, additional reaction steps for preparation of preferably compound (B) or (C) thus directly follow on from reaction step a1), without isolation of compound (A) from the reaction mixture, i.e. without the reaction step a2). This enables an even more rapid process regime in the preparation of indium-containing precursors.

The process according to the invention enables the preparation of compound (A) with a yield of preferably at least 70%, further preferably at least 75%, even further preferably at least 79% and very especially preferably of at least 85% and even more preferably more than 90% and even more preferably more than 95%. Yield figures given for the invention are always based on the theoretical yield.

The purity of the compound (A) prepared in accordance with the invention is preferably at least 95%, more preferably at least 98% and even more preferably more than 99%. Thus, preferably not more than 5%, more preferably not more than 2% and further preferably less than 1% of impurities, i.e. unwanted substances, are present in the compound (A) prepared.

A preferred compound (A) obtainable by the process according to the invention is selected from methylindium sesquichloride ($Me_3In_2Cl_3$), which, as described above, can also be regarded as a mixture of $Me_2InCl$ and $MeInCl_2$, and ethylindium sesquichloride ($Et_3In_2Cl_3$), which, as described above, can also be regarded as a mixture of $Et_2InCl$ and $EtInCl_2$. Most preferably, the process according to the invention is suitable for preparation of $Me_3In_2Cl_3$.

2. Further Processing of the Compound (A) to Give Indium-Containing Precursors

The compound (A) obtained by the process described above can optionally be processed further to give indium-containing precursors, preferably selected in accordance with the invention from compounds (B) and (C). The invention therefore also includes the use of the compound (A) prepared by the process according to the invention for preparation of indium-containing precursors, preferably selected from compound (B) and (C), for MOCVD or MOVPE processes.

The compound (A) prepared in accordance with the invention is particularly suitable for preparation of indium-containing precursors of the general formula:

i.e. compound (B), where R is a lower alkyl radical having 1 to 4 carbon atoms. The alkyl radical may be branched or unbranched, preferably unbranched. R is preferably selected from ethyl and methyl; in particular, R is methyl. By virtue of the process, R is determined by the R radical in compound (A), and so R in compound (A) corresponds to the R radical in compound (B).

Alternatively, the compound (A) prepared in accordance with the invention can be used to prepare indium-containing precursors of the general formula:

i.e. compound (C), where R is a lower alkyl radical having 1 to 4 carbon atoms, which may be branched or unbranched, and where R' is a nucleophilic radical other than R. R' is preferably selected from branched or unbranched and substituted or unsubstituted alkyl, branched or unbranched and substituted or unsubstituted aryl.

R' may especially be alkyl or phenyl substituted by branched or unbranched alkyl or alkoxy groups, or by amine radicals. In particular, R' is alkyl or aryl radicals having 1 to 6 carbon atoms, substituted by branched or unbranched alkyl or alkoxy groups, such as methyl, ethyl, n-butyl, propyl, sec-butyl, tert-butyl, isobutyl, isopropyl, cyclopropyl, cyclobutyl, methoxy, ethoxy, n-butoxy, propoxy, sec-butoxy, tert-butoxy, isobutoxy, isopropoxy, cyclopropoxy, cyclobutoxy, or else alkyl or aryl radicals which have 1 to 6 carbon atoms and are substituted (especially mono- or disubstituted) by amine radicals, themselves substituted by radicals of the branched or unbranched alkyl group type, such as methyl, ethyl, n-butyl, propyl, sec-butyl, tert-butyl, isobutyl, isopropyl, cyclopropyl, cyclobutyl.

The nucleophilic R' radical may, for example, be phenyl, tolyl, mesityl, dimethylamino, diethylamino, dibutylamino, diisopropylamino, $Et_2N—(CH_2)_3$, $Me_2N—(CH_2)_2$, $Me_2N—CH_2$, $Et_2N—(CH_2)_2$, $Et_2N—CH_2$, isopropyl, cyclopropyl, isobutyl, sec-butyl, tert-butyl, cyclopropyl, but especially propyl, n-butyl and ethyl or methyl. If the definitions of R and R' encompass the same radicals, R and R' in compound (C) must differ from one another. Thus, if R is methyl, R' must not be methyl.

In one embodiment of the invention, R is methyl and R' is an $Me_2N—(CH_2)_3$-radical. In a further embodiment of the invention, R is methyl and R' is ethyl. In a further embodiment of the invention, R is ethyl and R' is methyl. This results in the compounds $Me_2InEt$, $Et_2InMe$ and $Me_2In—(CH_2)_3—N-Me_2$ or $(CH_3)_2In—(CH_2)_3—N—(CH_3)_2$.

By virtue of the process, R is determined by the R radical in compound (A), such that R in compound (A) corresponds to the R radical in compound (C).

2.1. Further Processing of Compound (A) to Give Compound (B)

In preferred embodiments, the process for preparing the compound (A) is additionally followed by the following further reaction steps by which compound (B) is obtainable:

b1) reacting compound (A) with an alkyllithium to form lithium tetraalkylindate ($LiInR_4$), and isolating $LiInR_4$ from the reaction mixture, and b2) reacting the $LiInR_4$ with an indium chloride component to obtain compound (B).

Reaction step b2) may directly follow on from reaction step b1). Alternatively, reaction step b2) may also be effected with a time offset from reaction step b1).

Reaction Step b1):

Reaction step b1) comprises the reaction of compound (A) with an alkyllithium to form lithium tetraalkylindate, the lithium tetraalkylindate satisfying the following general formula:

$LiInR_4$ where R is as defined above. R is advantageously methyl or ethyl, especially methyl. By virtue of the process, R is determined by the R radical in compound (A).

The term "alkyllithium" encompasses those compounds which comprise at least one alkyl group and lithium. According to the invention, the alkyllithium preferably has the following general formula:

$RLi$ where R is as defined above. Most preferably, the alkyllithium is selected from ethyllithium (EtLi) and methyllithium (MeLi); the alkyllithium is especially methyllithium.

The alkyllithium is used in reaction step b1) as alkylating agent, but not as reducing agent.

Reaction step b1) preferably takes place in an organic solvent. Suitable organic solvents for step b1) are especially dialkyl ethers. Very particular preference is given to using a solvent selected from diethyl ether, diethoxymethane, methyltetrahydrofuran, longer-chain ethers and mixtures thereof in reaction step b1), longer-chain ethers being those comprising alkyl groups having more than 2 carbon atoms. Even more preferably, the solvent is diethyl ether or di-n-butyl ether, further preferably diethyl ether.

It has been found to be particularly advantageous to use between 4 and 5.3 equivalents of alkyllithium per equivalent of compound (A), more preferably between 4.8 and 5.3 equivalents and even more preferably between 4.8 and 5.2 equivalents, and most preferably about 5 equivalents.

In preferred embodiments, the alkyllithium is initially charged in the organic solvent and then compound (A) is added, preferably at temperatures between −10 and 10° C., further preferably at temperatures between −5 and 5° C., further preferably at −2 to 2° C. and even more preferably at 0+/−1° C. The reaction preferably takes place at temperatures between −30° C. and the boiling point of the organic solvent, further preferably at −5° C. to 35° C.

In alternative embodiments, compound (A) is initially charged in the organic solvent and the alkyllithium is subsequently added. This preferably involves adding the alkyllithium dropwise as a mixture with the organic solvent, more preferably at temperatures between −10 and 10° C., further preferably −5 and 5° C. and even further preferably at −2 to 2° C.

After all the reactants have been added, preference is given to stirring for preferably at least 10 min, further preferably at least 15 min. The reaction time is generally not more than 48 hours, preferably not more than 24 hours.

$LiInR_4$ is isolated from the reaction mixture. This is preferably done by removing the solvent and any by-products, especially LiCl, or residues of the reactants, preferably by distilling off volatile constituents and/or filtering the reaction mixture. Isolation of the $LiInR_4$ by filtration to remove LiCl and subsequent removal of the solvent by distillation has been found to be particularly advantageous.

In a preferred embodiment, the following reaction, in schematic form, proceeds in reaction step b1):

$$Me_3In_2Cl_3 + 5\,MeLi \xrightarrow{\text{diethyl ether}} 2\,LiInMe_4 + 3\,LiCl$$

Reaction Step b2):

Compound (B) is preparable from $LiInR_4$ by reaction of $LiInR_4$ with an indium chloride component.

According to the invention, the "indium chloride component" is a compound comprising indium and chloride. The term "indium chloride component", more particularly, also encompasses compounds which also comprise at least one alkyl radical as well as indium and chloride. The indium chloride component preferably has the following general formula:

$R_aIn_bCl_c$ where a is a number selected from 0, 1, 2 and 3 and b is a number selected from 1 and 2 and c is a number selected from 1, 2 and 3, and where a+b+c=4 or is a multiple of 4; more preferably, the sum of a, b and c=4 or 8. R is a lower alkyl radical having 1 to 4 carbon atoms. The alkyl radical may be branched or unbranched, preferably unbranched. R is preferably selected from ethyl and methyl; in particular, R is methyl.

Most preferably, the indium chloride component is selected from $InCl_3$, $R_2InCl$, $R_3In_2Cl_3$, $RInCl_2$ and mixtures thereof. Very particularly preferred indium chloride components are $R_2InCl$ or $R_3In_2Cl_3$, especially $Me_2InCl$, $Et_2InCl$, $Me_3In_2Cl_3$ or $Et_3In_2Cl_3$, further preferably $Me_2InCl$ or $Me_3In_2Cl_3$. Preferably, compound (A) is used as the indium chloride component, which makes the process according to the invention even less expensive. In particularly preferred embodiments, the indium chloride component is therefore $R_3In_2Cl_3$, i.e. compound (A). The indium chloride component is advantageously obtained by the above-described process steps a1) and a2).

The molar ratio of lithium tetraalkylindate to the indium chloride component may be between 1:1 and 3:1, preferably about 1:1, 2:1 or 3:1. In embodiments in which the indium chloride component is $R_2InCl$, a molar ratio of lithium tetraalkylindate to the indium chloride component of about 1:1 has been found to be particularly advantageous. In embodiments in which the indium chloride component is $R_3In_2Cl_3$, a molar ratio of lithium tetraalkylindate to the indium chloride component of about 3:1 is particularly advantageous. In embodiments in which the indium chloride component is $RInCl_2$, a molar ratio of lithium tetraalkylindate to the indium chloride component of about 2:1 is particularly advantageous.

The reaction of lithium tetraalkylindate with the indium chloride component can be effected in an organic solvent. Suitable organic solvents for step b2) are selected from alkanes including cyclic saturated hydrocarbons, aromatics, alcohols, ethers and cyclic ethers. Suitable organic solvents for step b2) have been found to be especially alkanes and aromatics, preferably selected from n-pentane, cyclohexane, n-decane, n-heptane, n-hexane, methylcyclohexane, n-nonane, n-octane and benzene, very particular preference being given to n-pentane.

In alternative embodiments, no organic solvent is used in reaction step b2), i.e. no organic solvent is used additionally as reaction medium. This has the advantage that any possible organic contaminations which restrict usability in compound (B) that result from partial breakdown of the solvent are avoided. Furthermore, this allows the process to be conducted in a more environmentally responsible manner. In one embodiment, step b2) is therefore performed in the absence of organic solvents.

Preferably, the $LiInR_4$ is initially charged in the reactor together with the indium chloride component. Subsequently, the organic solvent can be added. This is preferably followed by heating, preferably to temperatures between 30° C. and 120° C., further preferably to temperatures between 40° C. and 100° C. and even more preferably to temperatures between 50° C. and 90° C. Preference is given to maintaining such a temperature for at least 10 min and at most 24 hours, preferably for at least 30 min and at most 20 hours, further preferably at least 40 min and at most 12 hours and even more preferably for at least 90 min and at most 3 hours.

Subsequently, preference is given to cooling, preferably to a temperature of 25+/−5° C.

Preferably, compound (B) is then isolated from the mixture. The isolating of compound (B) preferably comprises the removing of the organic solvent and of compound (B) from the reaction mixture which may comprise salts, for example lithium chloride LiCl. This is especially effected by recondensation of organic solvent and compound (B) into a new vessel. For this purpose, all the volatile components such as compound (B) (i.e., for example, trimethylindium) are distilled off under reduced pressure together with the solvent from the residue (for example salts such as LiCl). Subsequently, the solvent is separated from compound (B), preferably by distilling it off under reduced pressure with preferably a residual gas pressure of less than 0.1 hPa, further preferably not more than 0.01 hPa, preferably into a cold trap at preferably −10° C.+/−5° C. Compound (B), for example trimethylindium or triethylindium, then remains in the vessel. Optionally, further purifying steps may follow, by purifying processes known to those skilled in the art. These further purifying steps may include the distillation, sublimation or recrystallization of compound (B).

In a preferred embodiment, the following reaction, in schematic form, proceeds in reaction step b2):

$LiInMe_4 + Me_2InCl \rightarrow 2Me_3In + LiCl$

In an alternative embodiment, in which the indium chloride component is compound (A), the following reaction, in schematic form, proceeds in reaction step b2):

$3LiInMe_4 + Me_3In_2Cl_3 \rightarrow 5Me_3In + 3LiCl$

The additional reaction steps comprising b1) and b2) enable the preparation of compound (B) from compound (A) with a yield of preferably at least 60%, further preferably at least 70%, even further preferably at least 75% and very especially preferably of 85% and even further preferably more than 90%. The purity of the compound (B) prepared in accordance with the invention is preferably at least 99%, more preferably at least 99.5% and more preferably more than 99.8%, and further preferably more than 99.999%. Especially in the case of performance of a further step for purifying the compound (B) prepared, preferably by sublimation of compound (B), a purity of >99.999% can be achieved.

2.2. Further Processing of Compound (A) to Give Compound (C)

In alternative embodiments, compound (A) is processed further to give compound (C), by adding additional further reaction steps onto the process according to the invention, comprising:

c1) separating dialkylindium chloride ($R_2InCl$) from compound (A), and c2) reacting $R_2InCl$ with an alkylating agent to form compound (C).

More preferably, compound (C) is dimethylaminopropyldimethylindium (DADI) or ethyldimethylindium ($Me_2InEt$).

In process step c1), dialkylindium chloride is separated from $R_3In_2Cl_3$, which, as described above, may also be regarded as a mixture of $R_2InCl$ and $RInCl_2$, the dialkylindium chloride being represented by the general formula $R_2InCl$ where R is as defined above and may advantageously be methyl or ethyl, especially methyl, where R is determined by the "R" radical in compound (A). $R_2InCl$ can be separated from compound (A) by sublimation. Preferably, compound (A) is heated for that purpose to temperatures between 150° C. and 200° C., further preferably between 155° C. and 195° C. and especially between 160° C. and 190° C. Optionally, the sublimation can also be effected under reduced pressure. In this case, a vacuum preferably with a residual gas pressure below 1 hPa, further preferably below 0.1 hPa, has been found to be useful. The person skilled in the art is aware that, in the case of performance of process step c) under vacuum, the separation of $R_2InCl$ can also be conducted at correspondingly lower temperatures. There is preferably a separation into a sediment and a sublimate, the sublimate preferably being $R_2InCl$.

By addition of an alkali metal halide, for example KCl, but also KF, or other MX with M=Na, K, Cs and X=F, Cl, Br, I), it is possible to distinctly enhance the yield in the sublimation and to completely separate $R_2InCl$.

In a preferred embodiment, the following reaction, in schematic form, proceeds in reaction step c1):

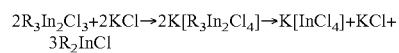

$2R_3In_2Cl_3 + 2KCl \rightarrow 2K[R_3In_2Cl_4] \rightarrow K[InCl_4] + KCl + 3R_2InCl$ Reaction step c1) is typically effected under protective gas, for example argon or nitrogen.

The alkylating agent in step c2) is especially selected from R'MgX, R'Li and R'$_3$Al where R' is as defined above. More preferably, the alkylating agent is Me$_2$N—(CH$_2$)$_3$-M where M is especially MgCl or Li or else ethyllithium (EtLi).

The conversion of R$_2$InCl to R$_2$InR', for example DADI, can be effected in an organic solvent by reaction with the alkylating agent, for example Me$_2$N—(CH$_2$)$_3$-M in the case of DADI. The organic solvent may be a dialkyl ether or a cyclic ether or mixtures thereof, especially diethyl ether or THF, further preferably THF.

Reaction step c2) is typically effected under protective gas.

Preferably, the alkylating agent is preferably initially charged in an organic solvent, especially THF, and then R$_2$InCl is added. In this case, R$_2$InCl is more preferably added dropwise as a mixture with the organic solvent, especially THF. The dropwise addition of R$_2$InCl is preferably effected gradually, more preferably over the course of at least 10 min, further preferably over the course of at least 20 min. The addition of R$_2$InCl is effected preferably at a temperature below 50° C., further preferably below 40° C. and more preferably at room temperature, i.e. 25° C.+/−5° C.

After all the reactants have been added, especially alkylating agent and R$_2$InCl, the mixture is preferably stirred. Preferably, the temperature in the course of stirring is below 50° C., further preferably below 40° C. and more preferably room temperature, i.e. 25° C.+/−5° C. Preference is given to stirring for at least 5 hours, further preferably for at least 10 hours. For reasons of cost, reaction times of 80 hours, further preferably 50 hours, are preferably not exceeded.

Subsequently, compound (C) is preferably isolated from the reaction mixture. The isolating of compound (C) may comprise the removal of the organic solvent, preferably under reduced pressure, and the separation of compound (B) from the reaction mixture by filtration and/or distillation.

The alkylating agents can be prepared by known processes, for example Me$_2$N—(CH$_2$)$_3$-M from 3-chloro-1-(dimethylamino)propane by reaction with magnesium turnings or lithium turnings. Typically, Me$_2$N—(CH$_2$)$_3$-M is prepared in an organic solvent, especially THF, while supplying heat. Optionally, iodine can be added for activation. Other known alkylating agents are commercially available.

By maintaining the conditions of the above-described preparation process for preparing compound (A) and optionally of the further processing to give indium-containing precursors, preferably selected from compounds (B) and (C), these compounds can be prepared in high yield and with high purity. The invention additionally includes the compound (A) prepared by the process, especially Me$_3$In$_2$Cl$_3$, and the indium-containing precursors obtainable therefrom, especially trimethylindium and dimethylaminopropyldimethylindium, and also R$_2$InCl.

Especially the high yield and purity, and also cost-effective and comparatively environmentally benign process selection, in the process according to the invention makes the process ideally suited to the industrial preparation of compound (A) or indium-containing precursors. More particularly, no pyrophoric intermediates form in accordance with the invention, which is particularly advantageous in the light of cost-effective and low-complexity preparation. The process according to the invention is especially characterized by particularly high indium exploitation. The overall indium conversion in the process according to the invention, based on the indium used, is preferably ≥ 70%, further preferably ≥75%, more preferably ≥80% and even more preferably >95%. The oxygen content in the compound (B) or (C) optionally obtainable, including indium alkoxides or oxides, is preferably <100 ppm (m/m), especially even <1 ppm (m/m).

A specific configuration relates to a process for preparing trialkylindium of the formula R$_3$In where R is an alkyl radical having 1 to 4 carbon atoms, the alkyl radical may be branched or unbranched and may especially be ethyl or methyl, comprising the steps of
preparing a compound (A) of the formula R$_3$In$_2$Cl$_3$ by reacting indium metal with an alkyl chloride of the formula RCl in the presence of an activator;
optionally isolating the compound (A);
reacting the compound (A) with an alkyllithium to form lithium tetraalkylindate LiInR$_4$, and isolating and optionally further purifying it;
reacting the lithium tetraalkylindate LiInR$_4$ with an indium chloride compound to give the trialkylindium of the formula R$_3$In;
optionally purifying the trialkylindium obtained.

A further specific configuration relates to a process for preparing trialkylindium of the formula R$_3$In where R is an alkyl radical having 1 to 4 carbon atoms, the alkyl radical may be branched or unbranched and may especially be ethyl or methyl, comprising the steps of
preparing a compound (A) of the formula R$_3$In$_2$Cl$_3$ by reacting indium metal with an alkyl chloride of the formula RCl in the presence of an activator;
optionally isolating the compound (A);
reacting the compound (A) with an alkyllithium to form lithium tetraalkylindate LiInR$_4$, and isolating and optionally further purifying it;
reacting the lithium tetraalkylindate LiInR$_4$ with an indium chloride compound to give the trialkylindium of the formula R$_3$In;
optionally purifying the trialkylindium obtained, where a compound (A) of the formula R$_3$In$_2$Cl$_3$ is used as activator, as indium chloride compound, or for the combination thereof.

A further specific configuration relates to a process for preparing trialkylindium of the formula R$_3$In where R is an alkyl radical having 1 to 4 carbon atoms, the alkyl radical may be branched or unbranched and may especially be ethyl or methyl, comprising the steps of
preparing a compound (A) of the formula R$_3$In$_2$Cl$_3$ by reacting indium metal with an alkyl chloride of the formula RCl in the presence of an activator;
optionally isolating the compound (A);
reacting the compound (A) with an alkyllithium to form lithium tetraalkylindate LiInR$_4$, and isolating and optionally further purifying it;
reacting the lithium tetraalkylindate LiInR$_4$ with an indium chloride compound to give the trialkylindium of the formula R$_3$In; where
the activator is not an indium halide InX$_3$ where X may be chlorine, bromine or iodine, and is not chlorine Cl$_2$, hydrogen chloride HCl, hydrogen H$_2$, iron chloride FeCl$_3$, (PtCl$_4$)$^{2-}$, PdCl$_2$, and the activator is not an oxide, especially In$_2$O, TiO$_2$, NiO$_2$ or Fe$_2$O$_3$,
optionally purifying the trialkylindium obtained.

A further specific configuration relates to a process for preparing an indium chloride component of the general formula:

$$R_a In_b Cl_c$$

where a is a number selected from 0, 1, 2 and 3 and b is a number selected from 1 and 2 and c is a number selected from 1, 2 and 3, and where a+b+c=4 or is a multiple of 4, the sum of a, b and c more preferably being 4 or 8, where R is an alkyl radical having 1 to 4 carbon atoms, the alkyl radical may be branched or unbranched and may especially be ethyl or methyl, comprising the steps of
  preparing a compound (A) of the formula $R_3In_2Cl_3$ by reacting indium metal with an alkyl chloride of the formula RCl in the presence of an activator;
  optionally isolating the compound (A); where
  the activator is not an indium halide $InX_3$ where X may be chlorine, bromine or iodine, and is not chlorine $Cl_2$, hydrogen chloride HCl, hydrogen $H_2$, iron chloride $FeCl_3$, $(PtCl_4)^{2-}$, $PdCl_2$, and the activator is not an oxide, especially $In_2O$, $TiO_2$, $NiO_2$ or $Fe_2O_3$; and where
  the indium chloride component may especially be: $R_2InCl$, $R_3In_2Cl_3$, $RInCl_2$ and mixtures thereof, or especially $Me_2InCl$, $Et_2InCl$, $MeInCl_2$, $EtInCl_2$, $Me_3In_2Cl_3$ or $Et_3In_2Cl_3$ (with Et=ethyl and Me=methyl).

A further specific configuration relates to a process for preparing trialkylindium of the formula $R_3In$ where R is an alkyl radical having 1 to 4 carbon atoms, the alkyl radical may be branched or unbranched and may especially be ethyl or methyl, including a process for preparing an indium chloride component of the general formula:

$$R_aIn_bCl_c$$

where a is a number selected from 0, 1, 2 and 3 and b is a number selected from 1 and 2 and c is a number selected from 1, 2 and 3, and where a+b+c=4 or is a multiple of 4, the sum of a, b and c more preferably being 4 or 8, where R is an alkyl radical having 1 to 4 carbon atoms, the alkyl radical may be branched or unbranched and may especially be ethyl or methyl, comprising the steps of
  preparing a compound (A) of the formula $R_3In_2Cl_3$ by reacting indium metal with an alkyl chloride of the formula RCl in the presence of an activator;
  optionally isolating the compound (A); where
  the activator is not an indium halide $InX_3$ where X may be chlorine, bromine or iodine, and is not chlorine $Cl_2$, hydrogen chloride HCl, hydrogen $H_2$, iron chloride $FeCl_3$, $(PtCl_4)^{2-}$, $PdCl_2$, and the activator is not an oxide, especially $In_2O$, $TiO_2$, $NiO_2$ or $Fe_2O_3$; and where
  the indium chloride component may especially be: $R_2InCl$, $R_3In_2Cl_3$, $RInCl_2$ and mixtures thereof, or especially $Me_2InCl$, $Et_2InCl$, $MeInCl_2$, $EtInCl_2$, $Me_3In_2Cl_3$ or $Et_3In_2Cl_3$ (with Et=ethyl and Me=methyl).

A further specific configuration relates to a process for preparing trialkylindium of the formula $R_3In$ where R is an alkyl radical having 1 to 4 carbon atoms, the alkyl radical may be branched or unbranched and may especially be ethyl or methyl, comprising the steps of
  preparing a compound (A) of the formula $R_3In_2Cl_3$ by reacting indium metal with an alkyl chloride of the formula RCl in the presence of an activator;
  optionally isolating the compound (A);
  reacting the compound (A) with an alkyllithium to form lithium tetraalkylindate $LiInR_4$, and isolating and optionally further purifying it;
  reacting the lithium tetraalkylindate $LiInR_4$ with an indium chloride compound to give the trialkylindium of the formula $R_3In$; where
  in the preparation of compound (A) 1.5 to 3 equivalents, especially 1.5 to 2.5 equivalents, of alkyl chloride per equivalent of indium are used.

A further specific configuration relates to a process for preparing an indium chloride component of the general formula:

$$R_aIn_bCl_c$$

where a is a number selected from 0, 1, 2 and 3 and b is a number selected from 1 and 2 and c is a number selected from 1, 2 and 3, and where a+b c=4 or is a multiple of 4, the sum of a, b and c more preferably being 4 or 8, where R is an alkyl radical having 1 to 4 carbon atoms, the alkyl radical may be branched or unbranched and may especially be ethyl or methyl, comprising the steps of
  preparing a compound (A) of the formula $R_3In_2Cl_3$ by reacting indium metal with an alkyl chloride of the formula RCl in the presence of an activator;
  optionally isolating the compound (A); where
  in the preparation of the indium chloride component 1.5 to 3 equivalents, especially 1.5 to 2.5 equivalents, of alkyl chloride per equivalent of indium are used.

A further specific configuration relates to a process for preparing trialkylindium of the formula $R_3In$ where R is an alkyl radical having 1 to 4 carbon atoms, the alkyl radical may be branched or unbranched and may especially be ethyl or methyl, comprising the steps of
  preparing a compound (A) of the formula $R_3In_2Cl_3$ by reacting indium metal with an alkyl chloride of the formula RCl in the presence of an activator;
  optionally isolating the compound (A);
  reacting the compound (A) with an alkyllithium to form lithium tetraalkylindate $LiInR_4$, and isolating and optionally further purifying it;
  reacting the lithium tetraalkylindate $LiInR_4$ with an indium chloride compound to give the trialkylindium of the formula $R_3In$; where
  in the preparation of compound (A) the addition of the alkyl chloride is effected at a constant gauge pressure of 1 bar to 4.5 bar, or 1.5 bar to 4 bar, or at 2 to 3.5 bar. The alkyl chloride is advantageously added by controlled introduction or injection of gaseous alkyl chloride.

A further specific configuration relates to a process for preparing an indium chloride component of the general formula:

$$R_aIn_bCl_c$$

where a is a number selected from 0, 1, 2 and 3 and b is a number selected from 1 and 2 and c is a number selected from 1, 2 and 3, and where a+b+c=4 or is a multiple of 4, the sum of a, b and c more preferably being 4 or 8, where R is an alkyl radical having 1 to 4 carbon atoms, the alkyl radical may be branched or unbranched and may especially be ethyl or methyl, comprising the steps of
  preparing a compound (A) of the formula $R_3In_2Cl_3$ by reacting indium metal with an alkyl chloride of the formula RCl in the presence of an activator;
  optionally isolating the compound (A); where
  in the preparation of the indium chloride component the addition of the alkyl chloride is effected at a constant gauge pressure of 1 bar to 4.5 bar, or 1.5 bar to 4 bar, or at 2 to 3.5 bar. The alkyl chloride is advantageously added by controlled introduction or injection of gaseous alkyl chloride.

A further specific configuration relates to a process for preparing trialkylindium of the formula $R_3In$ where R is an alkyl radical having 1 to 4 carbon atoms, the alkyl radical may be branched or unbranched and may especially be ethyl or methyl, comprising the steps of preparing a compound (A) of the formula $R_3In_2Cl_3$ by reacting indium metal with an alkyl chloride of the formula RCl in the presence of an activator;

optionally isolating the compound (A);

reacting the compound (A) with an alkyllithium to form lithium tetraalkylindate $LiInR_4$, and isolating and optionally further purifying it;

reacting the lithium tetraalkylindate $LiInR_4$ with an indium chloride compound to give the trialkylindium of the formula $R_3In$; where in the reaction of compound (A) with an alkyllithium 1 to 5 equivalents of alkyllithium per equivalent of compound (A) are used.

The indium-containing precursors optionally preparable by the process according to the invention, especially trimethylindium and dimethylaminopropyldimethylindium, because of their excellent purity, especially their very low oxygen content, are particularly suitable for MOCVD processes, for example for production of semiconductors or semiconductor components. The semiconductors or semiconductor components ultimately produced have various possible industrial uses. The invention therefore also includes the use of the compounds (B) and/or (C) optionally preparable in accordance with the invention as precursors for metal-organic chemical vapour deposition (MOCVD) or metal-organic vapour phase epitaxy (MOVPE).

WORKING EXAMPLES $Me_3In_2Cl_3$ (as compound A) was prepared by the process according to the invention. Compound (A) was also used to prepare $Me_3In$ as compound (B). In addition, dimethylaminopropyldimethylindium was prepared as compound (C).

1. Preparation of $Me_3In_2Cl_3$ 1.1. Reaction of Indium with Methyl Chloride to Form $Me_3In_2Cl_3$ with Activator (Molar Ratio of Indium to Activator: About 10:1)

2805 mg of indium (24.4 mmol) were initially charged in a 250 ml Parr bomb and admixed with a mixture of 275 mg of $InCl_3$ (1.24 mmol) and 200 mg of $Me_3In$ (1.25 mmol), and a magnetic stirrer bar. The Parr bomb was subsequently immersed into an oil bath heated to 220° C. for half an hour for homogenization. After cooling to room temperature, the Parr bomb was cooled to −200° C. and evacuated. Subsequently, at −200° C., 2582 mg of methyl chloride (51.1 mmol, 2.1 eq. based on indium) were condensed in and the Parr bomb was heated to 220° C. again. After one hour, all the indium had dissolved. During the reaction, a colourless solid sublimed onto the colder regions of the Parr bomb, which was conveyed into the reaction zone by repeated knocking on the Parr bomb. After cooling to room temperature, the excess methyl chloride was removed by applying vacuum and 4810 mg of $Me_3In_2Cl_3$, a colourless solid, were isolated (corresponding to 12.6 mmol of $Me_3In_2Cl_3$, removing the trimethylindium and $InCl_3$ used leaves 4335 mg/11.4 mmol/yield: 93% remaining).

1.2. Reaction of Indium with Methyl Chloride to Form $Me_3In_2Cl_3$ with Activator (Molar Ratio of Indium to Activator: About 177:1)

6.11 g of indium (53.2 mmol) and 60 mg of $InCl_3$ (0.3 mmol) were initially charged in a Parr bomb together with a stirrer bar. The Parr bomb was heated with a hot air gun until a distinct red/brown colour was apparent. Subsequently, the Parr bomb was cooled to room temperature under reduced pressure, and 5.99 g of MeCl (118.6 mmol) were condensed in at −196° C. After thawing to room temperature, the Parr bomb was immersed into an oil bath heated to 210° C. In the course of this, it was ensured that the temperature was in the range between 205° C. and 215° C. After 110 minutes, all the indium had dissolved and a clear colourless melt was observed. The Parr bomb was removed from the oil bath and all the volatile constituents were removed under reduced pressure. $Me_3In_2Cl_3$ was isolated as a colourless solid. Yield: 9.82 g (25.8 mmol, 97%).

1.3. Reaction of Indium with Methyl Chloride to Form $Me_3In_2Cl_3$ with Activator (Molar Ratio of Indium to Activator: About 4.7:1)

A 125 ml Parr bomb is initially charged with 860 mg of In (7.5 mmol) and 298 mg of $Me_3In_2Cl_3$ (0.8 mmol, from Example 1.1), along with a magnetic stirrer bar. After cooling to −200° C. and evacuating, 1.22 g of MeCl (24.2 mmol, 3.2 eq. based on indium) were condensed in and the Parr bomb is immersed into an oil bath preheated to 220° C. After one hour, the indium has dissolved completely. During the reaction, the deposition of a colourless solid on the colder walls of the vessel is observed. 1.505 g of $Me_3In_2Cl_3$ were isolated as a colourless solid (corresponding to 3.95 mmol, after removal of the $Me_3In_2Cl_3$ used: 1207 mg/3.2 mmol/84%).

1.4 Reaction of Indium with Methyl Chloride of $Me_3In_2Cl_3$ with Activator (Molar Ratio of Indium to Activator: About 10:1)

A 1 l pressure reactor is initially charged with 300 g (2.62 mol) of indium, which is melted at 160° C. under argon. While stirring, 49.92 g (0.13 mol) of $Me_3In_2Cl_3$ are added. The pressure reactor is first evacuated in order to remove argon, then MeCl is injected to 3 bar (absolute, 2 bar gauge). While stirring, the reaction mixture is heated to 200° C. At an internal temperature of about 185° C., the commencement of the reaction is evident by the start of gas absorption. The pressure is subsequently kept constant at 3 bar by replenishing MeCl. Even shortly after commencement of the reaction, the formation of a liquid phase atop the molten indium can be observed. The red colour of this solution indicates the presence of indium(I) compounds. The reactor is kept at a reaction temperature of 200° C. for 10 hours until the reaction mixture does not absorb any more MeCl and no liquid indium is evident in the reactor any longer. The pale yellow reaction solution is subsequently cooled to room temperature, in the course of which the product solidifies in the reactor, and the residual MeCl is removed from the reactor under reduced pressure. Subsequently, the product is liquefied again by heating under argon and discharged from the pressure reactor into a 1 l Schlenk flask. 539 g of $Me_3In_2Cl_3$ can be isolated as a colourless solid, corresponding to a yield of 98% (498 g, 1.28 mol,) based on the (metallic) indium used.

2. Further Processing of $Me_3In_2Cl_3$ to Give $Me_3In$ 2.1. Reaction of $Me_3In_2Cl_3$ with MeLi to Form $LiInMe_4$ 1430 mg of $Me_3In_2Cl_3$ (3.75 mmol, from Example 1.1) were added at 0° C. to 12 ml of a MeLi solution (1.565 mol/l in diethyl ether). After stirring at room temperature for about 1 h, the suspension was filtered without Celite and the filtrate was freed of the solvent. 1128 mg of a colourless solid were isolated (corresponding to 6.2 mmol of $LiInMe_4$, yield: 83%).

2.2. Reaction of $LiInMe_4$ with $Me_3In_2Cl_3$ to Form $Me_3In$ 947 mg of $LiInMe_4$ (5.2 mmol, from Example 2.1) and 660 mg of $Me_3In_2Cl_3$ (1.73 mmol, from Example 1.3) were initially charged in a 125 ml Parr bomb, and 10 ml of pentane were added. Subsequently, the Parr bomb was immersed into an oil bath preheated to 70° C. and stirred at that temperature for two hours. At 70° C., a clear liquid containing grey solids (LiCl and impurities) was observed, which solidified in the course of cooling to room temperature to become a crystal slurry. The volatile constituents of the Parr bomb were recondensed in a cold trap (RT→−78° C.), and then the pentane solvent was removed at −8° C. (sodium chloride/ice mixture) under fine vacuum. 980 mg of a colourless solid were isolated, which was contaminated only with traces of lithium chloride. Corresponding to 6.1 mmol/yield: 70% trimethylindium.

2.3. Reaction of LiInMe$_4$ with Me$_2$InCl to Form Me$_3$In 1079 mg of LiInMe$_4$ (5.9 mmol) and 1067 mg of Me$_2$InCl (5.9 mmol) were initially charged in a 125 ml Parr bomb, and 20 ml of pentane were added. Subsequently, the Parr bomb was immersed into an oil bath preheated to 70° C. and stirred at that temperature overnight. At 70° C., a slightly turbid suspension was observed, which solidified to become a crystal slurry as it cooled down to room temperature. The volatile constituents of the Parr bomb were recondensed in a cold trap (RT→−78° C.), and then the pentane solvent was removed at −8° C. (sodium chloride/ice mixture) under fine vacuum. 1591 mg of a colourless solid were isolated (10.0 mmol, yield: 81% trimethylindium).

3. Further Processing of Me$_3$In$_2$Cl$_3$ to Give dimethylaminopropyldimethylindium (DADI)

3.1. Separation of Me$_2$InCl from Me$_3$In$_2$Cl$_3$ by Sublimation 1050 mg (2.76 mmol) of Me$_3$In$_2$Cl$_3$ (from Example 1.4) were immersed into an oil bath at 170-180° C. in a Schlenk flask overnight. A colourless solid resublimed in the colder regions of the Schlenk flask. After cooling to room temperature, a cooled melt was observed at the base. Mass of the sublimed solid (Me$_2$InCl, identified via $^1$H NMR): 160 mg (0.89 mmol, yield: 32%). Mass of the cooled melt: 860 mg.

3.2 Separation of Me$_2$InCl from Me$_3$In$_2$Cl$_3$ by Sublimation in the Presence of KCl 1.60 g (4.20 mmol) of Me$_3$In$_2$Cl$_3$ (from Example 1.4) were melted together with 0.44 g (5.91 mmol) of KCl at 140° C. in a Schlenk flask equipped with a sublimation tube until a clear homogeneous melt was obtained. After cooling to room temperature, the whole system was evacuated to $10^{-3}$ mbar and the solidified melt was heated gradually to 190° C. In the course of this, the solid began to melt and, at the same time, the resublimation of a colourless solid was observed in the sublimation tube. After about two hours, the melt had been converted to a colourless solid and the sublimation was ended. From the sublimation tube, it was possible to obtain 1.12 g (6.22 mmol, yield: 99%) of Me$_2$InCl as a colourless solid, identified via $^1$H NMR.

3.3. Reaction of Me$_2$InCl with Dimethylaminopropyl-magnesium Chloride

A 500 ml three-neck flask was initially charged with 150 ml of dried THF and 5.26 g (216 mmol, 1.95 equiv.) of magnesium turnings, and the contents were heated to reflux.

After adding a spatula-tip of iodine to activate the magnesium, 15.55 g (126 mmol, 1.14 equiv.) of 3-dimethylaminopropyl chloride were slowly added dropwise and then the reaction mixture was heated under reflux for a further 2.5 h. After the reaction mixture had cooled to room temperature, 20.00 g (111 mmol) of Me$_2$InCl dissolved in 150 ml of dried THF were added dropwise within 30 minutes, and the resulting reaction solution was stirred at room temperature for 20 hours.

Subsequently, the THF was removed under reduced pressure, the residue was suspended in 100 ml of dried hexane and stirred at room temperature for 2 h, and the resulting white solid was removed by means of a reversible frit and washed twice with 50 ml each time of dried hexane. The clear filtrate was concentrated to dryness under reduced pressure and distilled at 80° C. and 5 mbar for purification. DADI was obtained as a clear liquid (19.7 g, 85.3 mmol, yield: 77%).

3.3. Reaction of Me$_2$InCl with 3-dimethylaminopropyl-lithium

A 500 ml three-neck flask was initially charged with 75 ml of dried THF and 1.16 g (170 mmol, 3 equiv.) of lithium turnings, and the contents were heated to reflux.

After attainment of reflux, 10.12 g (83.2 mmol, 1.5 equiv.) of 3-dimethylaminopropyl chloride were slowly added dropwise and then the reaction mixture was heated under reflux for a further 2.5 h. After the reaction mixture had cooled to room temperature, 10.00 g (55.4 mmol) of Me$_2$InCl dissolved in 75 ml of dried THF were added dropwise within 30 minutes, and the resulting reaction solution was stirred at room temperature for 20 hours.

Subsequently, the THF was removed under reduced pressure, the residue was suspended in 100 ml of dried pentane and stirred at room temperature for 2 h, and the resulting white solid was removed by means of a reversible frit and washed twice with 50 ml each time of dried pentane. The clear filtrate was concentrated to dryness under reduced pressure and distilled at 80° C. for purification. DADI was obtained as a clear liquid.

The invention claimed is:

1. A process for preparing a compound (A) of the general formula:

$$R_3In_2Cl_3$$

comprising:
reacting indium with an alkyl donor by adding alkyl donor at a temperature from 150° to 235° C. in the presence of an activator to form the compound (A), the alkyl donor being alkyl chloride (RCl), and
optionally isolating compound (A) from the reaction mixture,
wherein compound (A) comprises a mixture of dialkylindium chloride (R$_2$InCl) and alkylindium dichloride (RInCl$_2$) in a ratio ranging from 60:40 to 40:60, where R is methyl or ethyl,
wherein the alkyl donor is gaseous alkyl chloride,
wherein the alkyl chloride (RCl) is introduced at a constant gauge pressure, and
wherein the alkyl chloride (RCl) is introduced at a constant gauge pressure of 1 bar to 4.5 bar.

2. The process of claim 1, Wherein the activator is selected from the group consisting of dialkylindium chloride (R$_2$InCl), alkylindium dichloride (RInCl$_2$), a mixture of trialkylindium (R$_3$In) and InCl$_3$, compound (A), and mixtures thereof.

3. The process of claim 1, wherein 1.5 to 5 equivalents of alkyl donor per equivalent of indium donor are used.

4. The process of claim 1, wherein the reaction is carried out at a temperature of about 150° C. to about 250° C.

5. The process of claim 1, wherein compound (A) comprises a mixture of dialkylindium chloride (R$_2$InCl) and alkylindium dichloride (RInCl$_2$) in a ratio of 50:50.

6. A process for preparing a compound (A) of the general formula:

$$R_3In_2Cl_3$$

comprising:
reacting indium with alkyl chloride (RCl) in the presence of an activator to form the compound (A), and
optionally isolating compound (A) from the reaction mixture, wherein the activator is selected from the group consisting of compound (A), dialkylindium chloride (R$_2$InCl), alkylindium dichloride (RInCl$_2$), and mixtures thereof, wherein compound (A) comprises a mixture of dialkylindium chloride (R$_2$InCl) and alkylindium dichloride (RInCl$_2$) in a ratio ranging from 60:40 to 40:60, wherein the alky chloride (RCl) is introduced in gaseous form and at a constant gauge pressure of 1 bar to 4.5 bar, and where R is methyl or ethyl.

7. The process of claim 6, wherein compound (A) comprises a mixture of dialkylindium chloride (R$_2$InCl) and alkylindium dichloride (RInCl$_2$) in a ratio of 50:50.

8. The process of claim 6, wherein the reaction is carried of at a temperature of about 150° C. to about 250° C.

9. The process of claim 6, wherein 1.5 to 2.9 equivalents of alkyl donor per equivalent of indium donor are used.

10. The process of claim 6, wherein the purity of the compound (A) is at least 95%.

11. A process for preparing a compound (A) of the general formula:

comprising:

reacting indium with alkyl chloride (RCl) by adding alkyl donor at a temperature from 150° to 235° C. in the presence of an activator to form the compound (A), and optionally isolating compound (A) from the reaction mixture, wherein the activator is selected from the group consisting of compound (A), dialkylindium chloride (R$_2$InCl), alkylindium dichloride (RInCl$_2$), and mixtures thereof, wherein compound (A) comprises a mixture of dialkylindium chloride (R$_2$InCl) and alkylindium dichloride (RInCl$_2$) in a ratio ranging from 60:40 to 40:60, wherein the alkyl chloride (RCl) is added in gaseous form and at a constant gauge pressure of 1 bar to 4.5 bar, wherein the indium is present in liquid form and the addition of alkyl chloride is carried out at a temperature of 156° C. or more, and where R is methyl or ethyl.

12. The process of claim 11, wherein the reaction is carried out at a temperature of about 150° C. to about 250° C.

13. The process of claim 11, wherein compound (A) comprises a mixture of dialkylindium chloride (R$_2$InCl) and alkylindium dichloride (RInCl$_2$) in a ratio of 50:50.

14. The process of claim 11, wherein the alkyl chloride (RCl) is introduced at a constant gauge pressure of 2 bar to 4 bar.

15. The process of claim 11, wherein the reaction is carried out at a temperature of about 180° C. to about 230° C.

16. The process of claim 11, wherein 1.5 to 5 equivalents of alkyl donor per equivalent of indium donor are used.

* * * * *